United States Patent [19]

McLaughlin

[11] Patent Number: 5,094,619
[45] Date of Patent: Mar. 10, 1992

[54] COLORATION OF DENTAL RESTORATIONS

[76] Inventor: Gerald G. McLaughlin, 12 Cottonwood Ave., Port Jefferson Station, N.Y. 11776

[21] Appl. No.: 441,371

[22] Filed: Nov. 27, 1989

Related U.S. Application Data

[63] Continuation-in-part of Ser. No. 225,713, Jul. 28, 1988, abandoned, which is a continuation of Ser. No. 943,927, Dec. 17, 1986, abandoned.

[51] Int. Cl.$^5$ .................. A61C 13/08; A61K 6/00
[52] U.S. Cl. .................. 433/203.1; 106/35; 260/998.11; 264/20; 433/215; 433/217.1; 523/115; 523/122; 427/2
[58] Field of Search ............ 106/35; 260/998.11; 433/203.1, 215, 217; 264/20; 523/115, 116, 122; 427/2

[56] References Cited

U.S. PATENT DOCUMENTS

| | | | |
|---|---|---|---|
| 3,488,846 | 1/1970 | Cornell | 264/20 |
| 3,932,938 | 1/1976 | Mackta | 433/203.1 |
| 4,150,485 | 4/1979 | Lee, Jr. et al. | 523/115 |
| 4,261,879 | 4/1981 | Kemper | 260/998.11 |
| 4,433,959 | 2/1984 | Faunce | 106/35 |
| 4,481,227 | 11/1984 | Tanaka | 427/2 |
| 4,512,743 | 4/1985 | Santucci et al. | 523/115 |
| 4,563,153 | 1/1986 | Schaefer | 423/223 |
| 4,650,418 | 3/1987 | Blair et al. | 433/203.1 |
| 4,743,642 | 5/1988 | Yanacek et al. | 524/358 |

OTHER PUBLICATIONS

Pilkington, E. L., *Journal of the Amer. Dental Assoc.*, vol. XVI, May 1929, pp. 804–812.

*Primary Examiner*—Paul Lieberman
*Assistant Examiner*—Linda D. Skaling

[57] ABSTRACT

A method of coloring dental restorations which consists of incorporating within the dental restoration material prior to curing a coloration agent which upon the application of heat or other energy alters the color of the restoration. By applying the energy in steps it is possible to match closely the color of the restoration to adjacent teeth or that of the tooth on which the restoration is mounted.

20 Claims, No Drawings

COLORATION OF DENTAL RESTORATIONS

This application is a continuation-in-part of my application Ser. No. 07/225,713 filed on July 28, 1988, now abandoned, which is a continuation of Ser. No. 06/943,927 filed Dec. 17, 1986, now abandoned.

BACKGROUND OF THE INVENTION

This invention relates to the coloration of dental restorations and more particularly to methods of altering the coloring of previously prepared dental restorations to obtain a matching or otherwise desired color. By dental restoration herein is meant any configuration of material designed to improve the appearance or function of a tooth or teeth. This would include fillings, bridges, crowns, dentures, etc.

Present techniques for obtaining the desired color of restorations involve either having the coloring agent incorporated into the material itself at the time of formulation, or applying the coloring agent as a coating after the restoration has been manufactured. Typical of proposed methods of incorporating the coloring agent within the restoration material prior to preparing the restoration is shown in U.S. Pat. Nos. 4,433,959 and 4,563,153. U.S. Pat. No. 4,481,227 shows a method of adding the coloration agent to restoration after the latter is prepared.

Both of these methods have severe drawbacks. When the coloring agent is incorporated into the material, typically in the laboratory where the restoration is manufactured, it is difficult if not impossible to match the color and shading of the restoration perfectly with the tooth on which the crown is to be mounted. Coating techniques also generally require preparation in the laboratory with the similar difficulty to obtain an acceptable, if not a perfect, match. In both techniques, it is not possible or convenient to alter the color without repeating the complete procedure involved.

SUMMARY OF THE INVENTION

The present invention eliminates or reduces considerably the disadvantages and drawbacks of present methods of coloring dental restorations by making it possible for the dentist to alter the color or hue of a restoration just prior to mounting in order to match perfectly with adjacent teeth and the tooth which has been prepared for the restoration.

According to the principles of this invention, a material having the capability of having its color altered with the application of a stimulus is incorporated into the mixture of ingredients making up the restoration prior to its fabrication. The color of the restoration material after being cured is then altered with the application of the particular stimulus to obtain the desired color (that is, hue, chroma, or value). This may be accomplished in stages, for example, a slight change may be induced, and then the restoration is placed on the tooth to check the match. It will then be removed if the match is not acceptable, and a further change in color is induced. In addition, changes in color can be induced while the restoration is in place. Ultimately the dental practitioner is able to produce a perfect color match in the restoration which is then permanently installed on the tooth which has been prepared for it.

The type of stimulus required to induce the change in color depends upon the material which has been selected as the coloration agent. For example, many materials are color sensitive to the application of a stimulus consisting of heat. One such material is sucrose, a common variety of sugar generally derived from cane. The application of heat will cause this material to go through various shades of color, from yellow, to brown, and then to black, the rate and degree of color change being a function of the amount of heat applied (i.e., the temperature), the length of application of the heat, and the fineness or grain size of the sugar.

The heat may be applied in a variety of ways, for example, the use of a preheated oven, a heated probe, the application of infrared radiation, or the use of a laser beam.

The use of a material such as sucrose which gains color with the application of the stimulus (i.e., heat) is referred to herein as the color additive system or method.

Some materials lose color upon the application of the stimulus. Where such a material is employed in the present invention, the system or method is referred to as being subtractive. Where the material changes color, as opposed to either losing or gaining color, the method or system is described as variable.

By stimulus herein is meant any form of energy which induces the color change in the coloration agent or dye material being employed for that purpose. Hence, depending upon the dye material being employed, the stimulus may be heat, laser energy, visible light at specific wave lengths, ultra violet radiation, microwave radiation, x-rays, the application of cold, and other types of energy capable of inducing the type of color change which is desired. In the application of laser energy, by focusing that energy at point below the surface of the restoration, it is possible to obtain a color change within the restoration producing an effect more closely resembling that of the color in natural teeth.

By coloration agent or dye material herein is meant any material to be mixed with the dental restoration material having color properties of hue, chroma, or value not adversely affected by the process involved in curing the restoration material, and whose color properties of hue, chroma, or value are predictably changed by the application of an appropriate stimulus. The restoration material remains relatively stable as to its color properties once altered by the stimulus, and the restoration material is not adversely affected by the normal conditions or environment in which the restoration will remain in place.

In accordance with the principles of this invention, one preferred embodiment consists of a method of coloring a dental restoration which comprises the steps of incorporating into the mixture of ingredients from which the restoration is manufactured a coloration agent or dye material whose color is sensitive to the application of a stimulus, then manufacturing the restoration followed by subjecting the restoration to the stimulus to obtain a color to match perfectly with the color of adjacent teeth or the tooth on which the restoration is to be mounted permanently in place.

It is thus a principal object of this invention to provide a method of coloring a dental restoration capable of producing a better color match with the tooth on which the restoration is to be permanently mounted.

Other objects and advantages of this invention will become more obvious from the following description of the preferred embodiments of this invention.

DETAILED DESCRIPTION OF THE PREFERRED EMBODIMENTS

In the manufacture of fillings, crowns and other dental restorations, composition materials of polymerizable plastics are often employed. Typically, polymerization of the material once properly shaped is induced by either a chemical initiator such as a catalyst or the application of ultraviolet rays to the photosensitized mixture. As described in the previously noted U.S. Pat. No. 4,563,153 the color is obtained by incorporating into the mixture a pigment.

In accordance with the principles of this invention, in a preferred embodiment, a commercially available polymerizable composite for dental applications is mixed with a powdered coloration agent whose color, hue, or transparency is capable of being altered by the application of either heat, ultraviolet light, visible light, x-rays, microwaves, etc., but which is not affected by the process involved in curing the composite.

Polymerizable dental composites are well known in the art and consist of three primary parts, and the coloration agent in accordance with the principles of this invention is added to such a composite. Each dental composite consists of the polymer itself, the filler material or reinforcing particle mass, and a chemical or set of chemicals to create stability.

The present invention can work with any dental composite or other dental restoration material into which the coloration agent or pigment can be mixed, since it works independently of the chemistry involved, subject to the limitations described below. In effect, the dental restoration material acts only as a vehicle for the coloration agent.

In the case of the preparation of a crown, the dental composite or other dental restoration material as described above containing the coloration agent is used to coat a statue or model previously prepared according to standard dental practice and shaped to be mounted on the tooth. The coating is then cured according to the instructions of the manufacturer of the restoration material. Typically, the curing process would involve the use of light, or heat, or in some cases a chemical initiator which would be incorporated into the composite and would harden the mixture within a certain period of time.

The crown is then removed from the model of the tooth, and the dental practitioner would apply the appropriate stimulus to the crown to obtain the color or hue to match closely that of adjacent teeth or the tooth on which it is to be mounted. For example, if the coloration agent is one in which heat is required to adjust the shade of color, and heat was not instrumental in curing the composite on the model of the tooth, heat would be applied to the restoration to obtain the shade closely matching that of the tooth. This could be done in stages, until a perfect match with adjacent teeth is obtained. It should be noted that an electrically heated probe, for example, may be employed in order to obtain localized shading with color gradients if desired to obtain a more natural appearance.

The formed and properly colored restoration would then be cemented to the previously prepared tooth and the practitioner would smooth the finish of the crown to blend in with the tooth. This will result in a crown or restoration which is more perfectly matched in color to the tooth on which it is mounted and adjacent teeth than has been heretofore possible with techniques employed up to now.

A typical polymerizable dental composite in common use today and sold under a variety of trade names consists of a resin matrix or material such as dimethacrylate monomer, methyl methacrylate, or polyurethane mixed with low viscosity methacrylate monomers such as triethylene glycol dimethacrylate and containing stabilizers and one or more fillers such as pre-polymerized resin material, glass fibers, carbon fibers, ground crystalline quartz, calcium silicate, etc. The filler usually is treated with a coupling agent such as vinyl silane or gamma-methacryloxy propyl silane prior to its incorporation in the composite.

The most common organic matrix in use in recent years is the dimethacrylate monomer known in the industry as BIS-GMA which is described in "Dental Materials" by Craig et al., pub. 1987, The C.V. Mosby Company. Under some circumstances the restoration material may be porcelain or other material capable of being cured and containing the coloration agent.

The present invention involves three different types of color alterations depending upon the type of coloration agent to be employed.

Color Additive Method

In this method the coloration agent mixed in as filler with the dental composite is one which is devoid or lacking in color, such as white or translucent, and with the application of the stimulus takes on a color, going through various stages or colors, and at a rate of change which depends upon the nature of the material, the amount present in the composite, and grain size.

The following materials along with their pertinent characteristics have been found to be useful in this method:

a. Ordinary micro-pulverized, crystalline household cane sugar (sucrose). This material when mixed in with the composite in its extra fine state will darken upon the application of heat. At about 450 deg. F., this material passes through the following stages depending upon the length of time the heat is maintained: white, to transparent, to yellow, to orange, to red, to brown, and then to black.

b. Ordinary household sugar as above (sucrose) mixed with anhydrous copper sulfate has been found, upon the application of at least 400 deg. F. to change from white, to green, to dark brown, and then to intense black.

In the additive method, the color before the application of stimulus, i.e., heat, would be that of a translucent white nature, and after application of a suitable amount of heat the particles of the coloration agent would begin to break down or change, such as to become a yellow-brown. Thus, at the time of manufacture, the restoration would appear a normal tooth-colored white. With the application of heat, the particles would change in color and impart a yellow-brown color to the composite. The degree of color change in the restoration is controlled by the amount of heat applied, its concentration in the composite, and the grain size of the coloration agent.

The fineness or grain size of the coloration agent particles is not critical within the context of this invention. That is, it has been found that as long as the powdered agent is sufficiently fine to avoid a grainy appearance in the color of the restoration as finally altered, the only effect of changing grain size is to alter the rate of time at which the color changes during the application of the stimulus. Thus, it has been found that the finer the coloration agent is, the faster the color will change with the application of the stimulus. Hence, in order to obtain with a higher degree of accuracy the color desired, extra fine coloration agent particles are to be avoided in order to prevent the color change from taking place too fast.

Similarly, it has been found that the amount of agent is not critical in terms of this invention. That is, while only a very small (i.e., trace) amount of coloration agent is required to carry out this invention, the effect of increasing or decreasing the actual amount of agent being employed is to effect only the rate at which the color change takes place upon application of the stimulus. The more agent which is added, the faster this color change will take place.

Heating of the agent within the composite material is accomplished by the use of a laser beam, placement in an oven or heated glass beads, or any one of a number of available methods, including an electrically heated element or probe as mentioned earlier.

EXAMPLE 1

About 37 mg. of basic dental composite material, sufficient for the crown of a single tooth, is separated out from an injector containing this material. This material is sold by the 3M Corp. and is identified as P30. (Other companies sell similar materials.)

Then a trace amount or a pinch amount of ultra fine sucrose is mixed in thoroughly with the composite material. The sugar is measured out by pressing the tip of a spatula against a mound of sugar, and the sugar which adhered to the surface of the spatula (that is, one layer) is scraped or wiped off into the composite material.

A crown is then formed from the thoroughly mixed composite material in a conventional manner and cured with the application of light from a source in accordance with the recommendations of the manufacturer of the composite. It has been found that the presence of the sugar does not alter noticeably the curing characteristics of the composite.

Then the cured crown is fitted on its tooth and an observation made as to how much color is needed to be added. The crown is removed and inserted into an oven preheated to 450 deg. F. The crown is removed after a few seconds and placed again on the tooth with its coloration observed. The crown is returned to the oven for a few seconds and the process repeated until the exact color desired is obtained. Then the crown is permanently mounted.

EXAMPLE 2

The steps described in the previous example are repeated except that trace amounts of the sugar are mixed in equal proportions by volume with powdered anhydrous copper sulfate before mixing with the composite. The preheated oven is set at 400 deg. F. to obtain the desired color change. The use of the mixture of sugar and copper sulfate gives certain color shades not obtainable with the use of sugar alone.

Color Subtractive Method

In this method, the coloration agent or dye material is one which loses its color upon the application of the stimulus.

The following materials along with their pertinent characteristics have been found to be useful in this method:

The food colors known as HANSA yellows and Red No. 112 (also known as Fanchon Fast Red sold by Mobay Chemical Co., Catalog No. R6211), which range in color from red-yellow, green-yellow, to red. When heated to about 350 deg. F., they gradually lose their color and become translucent and then transparent.

Fanchon Yellow (Mobay Chemical Co., YH5790), which turns from a yellow to an orange when heated in the 550 deg. F. range. This agent is included in the subtractive method because when it is employed in the composite, it fades away, turning from a yellow to a white.

When the subtractive method is employed, the prepared restoration would, typically, be a yellow-brown to start out with, and with the application of the stimulus, such as heat, the color would gradually be lightened to obtained the desired shade.

EXAMPLES 3 and 4

The steps described in Example 1 are repeated utilizing in each case first Red No. 112 and then Fanchon Yellow, each in trace amounts. The remaining steps are all the same except that in successive applications of heat the color gradually disappears until the desired shade is reached. Oven temperatures are those indicated above for these materials.

Variable Method

In this method, the coloration agent or dye material selected is one which changes from one color to another as a result of the application of the appropriate stimulus.

The following materials have been found to be useful in this method:

D&C Red #21 aluminum lake manufactured by Sun Chemical Co., New York, which starts out as a red and changes in stages to orange, then to brown, and finally black when heated at about 500 deg. F.

Powdered yellow iron oxide manufactured by Smith Chemical Company, and designated as #420. When heated at 400 deg. F. it changes to a red brown color.

Powdered black iron oxide manufactured by Smith Chemical Company, and designated as #318. When heated at 400 deg. F. this material changes to a brown red color, thus a darker color than the yellow iron oxide.

The variable method has particular application where it is desirable to have a color throughout the material, but where the final desired color may not be known at the time of manufacture. It is now possible to mill dental restorations such as crowns out of ceramic, plastic or composite blocks. Unfortunately, it is not feasible to manufacture the blocks with the correct amount of coloration in exactly the right places for its eventual use, since this will vary from tooth to tooth. It would be possible, however, to manufacture the blocks with the color throughout the block, and allow the dentist or technician to alter the color intensity or hue in specific areas through the use of a laser, for example.

The crown could be milled from a block of composite which is of the correct color, but where the degree of intensity of the color is not exact. After the crown is milled, the dentist could apply laser energy to the area around the gumline to darken the shade and give a more lifelike appearance.

EXAMPLES 5, 6 and 7

Example 1 is repeated with each of the preceding three materials utilizing the heating temperatures indicated for the particular materials. Trace amounts of the coloration agents are employed as described with the resulting color changes indicated for each of the materials.

From the above description of the preferred embodiments of this invention it will be seen that there has been provided a method of coloring dental restorations such as crowns which permits accurate shading of the restorations to match existing colors in the environment and accomplishing this result in a manner far simpler and more economically than methods which have heretofore been in use or known.

Another advantage of this invention is that it lends itself to use in new methods of dental restorations in which the crowns or other restorations are accomplished using recently developed automated equipment for that purpose. With the use of such new equipment and newly developed techniques for accurately and mechanically registering the shade of a tooth in the mouth, a block of material is selected having the proper shade range. Then the shade can be registered by use of a fiberoptic probe connected to a computer terminal. A laser or heat tip is then activated, and the shade re-taken after a first adjustment of color in accordance with this invention is completed. This process could be repeated until the proper shade is achieved.

While only certain preferred embodiments of this invention have been described, it is understood that many variations of this invention are possible without departing from the principles of this invention as defined in the claims which follow.

What is claimed is:

1. A method of effecting the coloration of a restoration to be mounted on a tooth comprising the steps of:
   (a) incorporating into a dental composite which comprises a material selected from the group consisting of dimethacrylate monomer, methyl methacrylate, and polyurethane mixed with a methyacrylate monomer a coloration agent whose color changes when subject to the application of heat;
   (b) manufacturing said restoration from said dental composite without the application of heat; and
   (c) subjecting to repeated successive exposures at least a portion of said restoration to heat in a plurality of steps while placing said restoration on said tooth between each successive exposure of heat until the color of said restoration matches accurately a pre-selected color, followed by mounting said restoration.

2. The method of claim 1 wherein a trace amount of said coloration agent is added to said mixture.

3. The method of claim 1 wherein said coloration agent consists of a micro-pulverized crystalline sugar.

4. The method of claim 1 wherein said coloration agent comprises a mixture of micro-pulverized crystalline sugar and anhydrous copper sulfate.

5. The method of claim 1 wherein said coloration agent comprises yellow iron oxide.

6. The method of claim 1 wherein said coloration agent comprises black iron oxide.

7. A method of effecting the coloration of a restoration to be mounted on a tooth comprising the steps of:
   a. incorporating into a polymerizable mixture from which the restoration is manufactured a coloration agent selected from the class of materials which change color upon the application of heat, said polymerizable mixture selected from the group consisting of dimethacrylate monomer, methyl methacrylate, and polyurethane mixed with a methacrylate monomer;
   b. shaping said mixture into said restoration without the application of heat;
   c. polymerizing without the application of heat said mixture using a polymerizing agent which does not affect the color of said coloration agent; and
   d. subjecting to repeated successive exposures at least a portion of said restoration to heat in a plurality of steps while placing said restoration on said tooth between each successive exposure of heat until the color of said restoration matches accurately a pre-selected color followed by mounting said restoration permanently in place.

8. The method of claim 7 wherein said coloration agent is yellow iron oxide.

9. The method of claim 7 wherein said coloration agent is black iron oxide.

10. A method of effecting the coloration of a dental restoration comprising the steps of:
    (a) incorporating into a polymerizable mixture from which the restoration is manufactured a coloration agent consisting of micro-pulverized crystalline sugar in an amount sufficient to cause a change in color upon the application of heat, said polymerizable mixture selected from the group consisting of dimethacrylate monomer, methyl methacrylate, and polyurethane mixed with a methacrylate monomer;
    (b) shaping said mixture into said restoration;
    (c) polymerizing said mixture using a polymerizing agent which does not affect the color of said coloration agent; and
    (d) subjecting at least a portion of said restoration to sufficient heat for a sufficient length of time to change the color of said restoration to match accurately a pre-selected color.

11. The method of claim 10 wherein a trace amount of said sugar is incorporated into said mixture, the fineness of said sugar being sufficient to obtain a uniform visible color in said restoration upon application of said heat.

12. A method of effecting the coloration of a dental restoration comprising the steps of:
    a. incorporating into a polymerizable mixture from which the restoration is manufactured a trace amount of a coloration agent which is sufficient to change color upon the application of heat, said coloration agent consisting of a mixture of micro pulverized crystalline sugar and anhydrous copper sulfate in about equal volumes, said polymerizable mixture selected from the group consisting of dimethacrylate monomer, methyl methacrylate, and polyurethane mixed with a methacrylate monomer;
    b. shaping said mixture into said restoration;
    c. polymerizing said mixture using a polymerizing agent which does not affect the color of said coloration agent; and
    d. subjecting at least a portion of said restoration to sufficient heat for a sufficient length of time to change the color of said restoration to match accurately a pre-selected color.

13. The method of effecting the coloration of a restoration to be mounted on a tooth comprising the steps of:

a. incorporating into a polymerizable mixture from which the restoration is manufactured a coloration agent consisting of micro-pulverized crystalline sugar, said polymerizable mixture selected from the group consisting of dimethacrylate monomer, methyl methacrylate, and polyurethane mixed with a methacrylate monomer;
b. shaping said mixture into said restoration;
c. polymerizing said mixture using a polymerizing agent which does not affect the color of said coloration agent; and
d. subjecting at least a portion of said restoration to heat in a plurality of steps while placing said restoration on said tooth between each application of heat until the color of said restoration matches accurately a pre-selected color followed by mounting said restoration permanently in place.

14. The method of claim 13 wherein a trace amount of said sugar is incorporated into said mixture, the fineness of said sugar being sufficient to obtain a uniform visible color in said restoration after application of said heat.

15. The method of effecting the coloration of a restoration to be mounted on a tooth comprising the steps of:
a. incorporating into a polymerizable mixture from which the restoration is manufactured a coloration agent consisting of a mixture of micro pulverized crystalline sugar and anhydrous copper sulfate in about equal volumes in a trace amount, said polymerizable mixture selected from the group consisting of dimethacrylate monomer, methyl methacrylate, and polyurethane mixed with a methacrylate monomer;
b. shaping said mixture into said restoration;
c. polymerizing said mixture using a polymerizing agent which does not affect the color of said coloration agent; and
d. subjecting at least a portion of said restoration to heat in a plurality of steps while placing said restoration on said tooth between each application of heat until the color of said restoration matches accurately a pre-selected color followed by mounting said restoration permanently in place.

16. The method of effecting the coloration of a polymerizable dental restoration to be mounted on a tooth comprising the steps of:

a. incorporating into a dental composite comprising an unsaturated polymerizable monomer from which the restoration is manufactured a coloration agent selected from the class of materials which change color upon the application of heat;
b. shaping said mixture into said restoration;
c. polymerizing said mixture without the application of said heat using a polymerizing agent which does not affect the color of said coloration agent; and
d. subjecting to repeated successive exposures at least a portion of said restoration to said heat in a plurality of steps while said restoration is on said tooth until the color of said restoration matches accurately the color of an adjacent tooth followed by mounting said restoration permanently in place.

17. The method of effecting the coloration of a dental restoration to be mounted on a tooth comprising the steps of:
a. incorporating into a polymerizable dental restorative material containing an unsaturated polymerizable monomer from which the restoration is manufactured a coloration agent selected from the class of materials which change color upon the application of heat;
b. shaping said mixture into said restoration;
c. curing said mixture using an agent which does not affect the color of said coloration agent;
d. subjecting said restoration after curing to repeated successive exposures of said heat in a plurality of steps until the color of said restoration matches accurately a preselected color; and
e. mounting said restoration permanently in place on said tooth.

18. The method of claim 17 in which said restoration is removed for exposure to said heat and is mountable on said tooth between the successive exposures of said heat.

19. The method of claim 17 in which said restoration is mounted on said tooth during the successive exposures of said heat so that the color of said restoration is altered while said restoration is mounted.

20. The method of claim 17 in which said preselected color is the color of an adjacent tooth so that said successive exposures are continued until the color of said restoration approaches and matches that of said adjacent tooth.

* * * * *